United States Patent
Marx

(10) Patent No.: US 9,610,192 B2
(45) Date of Patent: Apr. 4, 2017

(54) AUTOMATED INCREMENTAL EYEDROP DELIVERY SYSTEM WITH EYELID RETRACTING LEGS

(76) Inventor: Alvin J. Marx, San Antonio, TX (US)

( * ) Notice: Subject to any disclaimer, the term of this patent is extended or adjusted under 35 U.S.C. 154(b) by 314 days.

(21) Appl. No.: 13/582,463

(22) PCT Filed: Mar. 11, 2011

(86) PCT No.: PCT/US2011/028235
§ 371 (c)(1),
(2), (4) Date: Sep. 4, 2012

(87) PCT Pub. No.: WO2011/113028
PCT Pub. Date: Sep. 15, 2011

(65) Prior Publication Data
US 2013/0006202 A1     Jan. 3, 2013

Related U.S. Application Data

(63) Continuation-in-part of application No. 12/722,340, filed on Mar. 11, 2010, now Pat. No. 8,734,408.
(Continued)

(51) Int. Cl.
*A61M 35/00* (2006.01)
*A61F 9/00* (2006.01)

(52) U.S. Cl.
CPC .......... *A61F 9/0026* (2013.01); *A61F 9/0008* (2013.01)

(58) Field of Classification Search
CPC ............................. A61F 9/0026; A61F 9/0008
(Continued)

(56) References Cited

U.S. PATENT DOCUMENTS

| 1,362,682 A | 12/1920 | Dayton |
| 2,219,604 A | 10/1940 | Trotter |

(Continued)

FOREIGN PATENT DOCUMENTS

JP      2007215962 A    8/2007

*Primary Examiner* — Philip R Wiest
*Assistant Examiner* — Ariana Zimbouski
(74) *Attorney, Agent, or Firm* — Kammer Browning PLLC

(57) ABSTRACT

An eyedrop bottle holder with resilient arms formed from an inverted U-shaped band made from resilient injection molded plastic. The top middle portion of the inverted U-shape band includes a centrally located opening through which the top (dispensing portion) of a standard eyedrop bottle containing eyedrop solution may be positioned and held. The right and left arms of the U-shape band each terminate in an outwardly disposed J-shape foot, the underside of which is covered by a soft rubber-like pad. When a user inserts a standard eyedrop bottle into the holder, the dispensing tip of the eyedrop bottle may be positioned in close proximity to the user's eye. The user may cause his or her eye lid to remain open by using the fingers of one hand to squeeze the right and left arms of the holder together, then placing the pad of one arm on the upper ridge of the orbital eye socket and the pad of the second arm on the lower ridge of the orbital eye socket. Releasing the arms causes the skin of the user's upper and lower eyelids to be spread apart from each other and remain spread during an eyedrop solution dispensing event. The eyedrop bottle is retained within a housing that includes an electromechanical assembly with a rotating cam that pushes on the side of the bottle until a predetermined amount of solution is dispensed. When a set amount of eyedrop solution has been dispensed, the assembly resets itself. An electronic sensor detects the passage of a drop of solution from the bottle and directs a reverse motion to the rotating cam. Tilt sensors assist the user in (Continued)

properly orienting the device for use. An adaptor may be used to accommodate non-standard sized eyedrop bottles.

19 Claims, 12 Drawing Sheets

Related U.S. Application Data which is a continuation-in-part of application No. 12/319,908, filed on Jan. 12, 2009, now Pat. No. 8,246,589.

(60) Provisional application No. 61/097,153, filed on Sep. 15, 2008, provisional application No. 61/086,436, filed on Aug. 5, 2008, provisional application No. 61/075,768, filed on Jun. 26, 2008, provisional application No. 61/026,471, filed on Feb. 5, 2008.

(58) Field of Classification Search
USPC .................. 604/294–303, 521; 351/208–212
See application file for complete search history.

(56) References Cited

U.S. PATENT DOCUMENTS

| | | | |
|---|---|---|---|
| 2,734,665 A | 2/1956 | Flamm | |
| 3,261,355 A | 7/1966 | Burbig | |
| 3,486,663 A | 12/1969 | Humphrey | |
| 3,602,217 A * | 8/1971 | Felton et al. | 601/72 |
| 3,872,866 A | 3/1975 | Lelicoff | |
| 3,934,590 A | 1/1976 | Campagna et al. | |
| 4,085,750 A | 4/1978 | Bosshold | |
| 4,111,200 A | 9/1978 | Sbarra et al. | |
| 4,115,042 A | 9/1978 | Schroeder | |
| 4,131,115 A | 12/1978 | Peng | |
| 4,321,916 A | 3/1982 | McKee | |
| 4,336,895 A | 6/1982 | Aleff | |
| 4,349,133 A | 9/1982 | Christine | |
| 4,386,608 A | 6/1983 | Ehrlich | |
| 4,515,294 A | 5/1985 | Udall | |
| 4,531,944 A * | 7/1985 | Bechtle | 604/302 |
| 4,543,096 A | 9/1985 | Keene | |
| 4,722,372 A * | 2/1988 | Hoffman et al. | 141/98 |
| 4,834,727 A | 5/1989 | Cope | |
| 4,927,062 A | 5/1990 | Walsh | |
| 4,973,322 A | 11/1990 | Jewart | |
| 4,981,479 A | 1/1991 | Py | |
| 5,040,706 A | 8/1991 | Davis et al. | |
| 5,064,420 A * | 11/1991 | Clarke et al. | 604/295 |
| 5,215,231 A | 6/1993 | Paczonay | |
| 5,261,571 A | 11/1993 | Goncalves | |
| 5,370,267 A | 12/1994 | Schroeder | |
| 5,382,243 A | 1/1995 | Mulholland | |
| 5,401,259 A | 3/1995 | Py | |
| 5,516,008 A | 5/1996 | Rabenau et al. | |
| 5,578,020 A | 11/1996 | Mosley | |
| 5,611,464 A | 3/1997 | Tsao et al. | |
| 5,658,065 A * | 8/1997 | Jamieson | 362/106 |
| 5,795,342 A | 8/1998 | Shapiro et al. | |
| 5,902,292 A | 5/1999 | Feldman | |
| 5,982,289 A * | 11/1999 | Kingsley et al. | 340/609 |
| 5,993,428 A | 11/1999 | Hardge | |
| 6,010,488 A | 1/2000 | Deas | |
| 6,041,978 A | 3/2000 | Hagele | |
| RE37,047 E | 2/2001 | Py | |
| 6,241,124 B1 | 6/2001 | Hoyt | |
| 6,371,945 B1 | 4/2002 | Sherman | |
| 6,595,970 B1 | 7/2003 | Davidian | |
| 6,610,036 B2 | 8/2003 | Branch et al. | |
| 6,730,066 B1 | 5/2004 | Bennwik et al. | |
| 6,736,802 B1 | 5/2004 | Recanati | |
| 6,814,265 B2 | 11/2004 | Clifford et al. | |
| 7,191,916 B2 | 3/2007 | Clifford et al. | |
| 7,235,065 B1 | 6/2007 | Sorensen | |
| 7,513,396 B2 | 4/2009 | Pardes et al. | |
| 7,621,273 B2 | 11/2009 | Morton et al. | |
| 7,852,551 B2 * | 12/2010 | Hara et al. | 359/368 |
| 2004/0039355 A1 | 2/2004 | Gonzalez et al. | |
| 2004/0111070 A1 | 6/2004 | Hanley | |
| 2004/0173642 A1 | 9/2004 | Clifford et al. | |
| 2005/0131358 A1 | 6/2005 | Skolik | |
| 2005/0133543 A1 * | 6/2005 | Clifford et al. | 222/420 |
| 2005/0147546 A1 | 7/2005 | Long | |
| 2005/0261641 A1 | 11/2005 | Warchol | |
| 2006/0079851 A1 | 4/2006 | Guerrieri | |
| 2006/0264855 A1 | 11/2006 | Goldenberg et al. | |
| 2007/0055208 A1 | 3/2007 | Berger et al. | |
| 2007/0095862 A1 | 5/2007 | Swiss et al. | |
| 2008/0233053 A1* | 9/2008 | Gross et al. | 424/45 |
| 2009/0234302 A1* | 9/2009 | Hoendervoogt et al. | 604/288.01 |
| 2009/0236374 A1 | 9/2009 | Pardes et al. | |
| 2009/0259204 A1* | 10/2009 | Galdeti et al. | 604/302 |
| 2009/0293870 A1 | 12/2009 | Brunnberg et al. | |
| 2009/0318883 A1 | 12/2009 | Sugahara et al. | |
| 2010/0286633 A1 | 11/2010 | Marx | |

\* cited by examiner

AUTOMATED INCREMENTAL EYEDROP DELIVERY SYSTEM WITH EYELID RETRACTING LEGS

BACKGROUND OF THE INVENTION

1. Field of the Invention

The present invention relates generally to the field of eyedrop dispensing devices. The present invention relates more specifically to devices for facilitating the proper positioning of an eyedrop bottle and the automated dispensing of a quantity of eyedrop solution.

2. Description of the Related Art

Devices for dispensing eyedrop solutions are known. Generally, a bottle of eyedrop solution includes a drop dispenser that is built into the exit orifice of the container. To dispense the solution, the user squeezes the bottle forcing solution out of the exit orifice and into his or her eye. Many users have trouble with dispensing eyedrops from standard dispensing bottles. The user has a tendency to blink when the drop is about to enter the eye, causing the drop to miss the eye and land on a closed lid. Therefore, eyedrop solution is frequently wasted due to the user blinking during the attempted application and the user ends up with eyedrop solution streaming down his or her face. Problems also occur when the user dispenses too much eyedrop solution (too many drops) accidentally and when the user thinks they have dispensed a drop of solution when they have not.

A number of efforts have attempted to resolve the above mentioned problem. Thomas Keen, in his U.S. Pat. No. 4,543,096, discloses a dispenser with an eyelid opening device. The user is required to place a pair of lid spreading arms dangerously close to the eye and then press a lever arm to keep the eyelids apart. Thomas Sherman, in his U.S. Pat. No. 6,371,945, discloses an attachment for a bottle that includes a ring intended to help align the bottle with the eye. However, no attempt is made to hold the eyelid open. Gary Campagna, in his U.S. Pat. No. 3,934,590, shows a tripod like device for aligning the solution bottle over the user's eye. No attempt is made to hold the lid open. James Davidian, in his U.S. Pat. No. 6,595,970, shows a device for dispensing eye drops. He proposes a dispensing arm, one side of which includes an indentation that receives the user's nose, the other side of which accepts a dispensing bottle. The bottle includes a pair of arms which, when squeezed, impinge on the side walls of the bottle forcing solution out of the bottle and into the user's eye. No attempt is made to hold the user's eyelid open. U.S. Pat. No. 7,191,916 issued to Julia Clifford et al. shows a dispenser that attempts to control the amount of drops that exit a solution holding bottle. The bottle has retractable apertures that capture and release a drop of solution. The devices disclosed in U.S. Pat. No. 4,927,062 (Walsh); U.S. Pat. No. 6,041,978 (Hagele); U.S. Pat. No. 6,010,488 (Deas); and U.S. Pat. No. 4,834,727 (Cope) as well as U.S. Pat. No. 5,902,292 (Feldman), all attempt to position an eyedrop bottle in a correct location above a person's eye, but none include a means to help hold the user's eye lids spread apart in an open position. U.S. Pat. No. 4,321,916 (McKee) discloses an eyelid retractor that is used during ocular surgery or the like. It is not designed to be used with the dispensing of eyedrop solution.

None of the above cited devices safely holds the user's eyelids open while dispensing eyedrops from a standard eyedrop bottle. Additionally, none of the above mentioned patents describe a device that allows the user to dispense a portioned amount of eyedrop solution in an automatic and repeatable fashion. None of the above cited inventions dispenses a precise amount of eyedrop solution and simultaneously holds the user's eyelids open while doing so.

SUMMARY OF THE INVENTION

A primary object of the present invention is to provide a holder for an eyedrop bottle that facilitates the proper positioning of the bottle over the eye and includes resilient lid spreading legs.

Another object of the present invention is to provide a lid spreading eyedrop bottle holder that allows the user to easily attach and detach a standard eyedrop bottle to the lid spreading device.

Another object of the present invention is to provide a lid spreading eyedrop bottle holder that does not interfere with the eyedrop bottle tip and at the same time prevents the bottle tip from contacting the eye during proper use.

A further object of the present invention is to provide a lid spreading eyedrop bottle holder that firmly attaches to the eyedrop bottle and orients the bottle for dispensing.

Yet another object of the present invention is to provide a lid spreading eyedrop bottle holder that is inexpensive to manufacture.

Another object of the present invention is to provide a lid spreading eyedrop bottle holder that automatically dispenses a portioned amount of eyedrop solution when the user presses a dispensing button on the device.

Other objects and advantages of the present invention will become apparent from the following descriptions, taken in connection with the accompanying drawings, wherein, by way of illustration and example, an embodiment of the present invention is disclosed.

In accordance with a first preferred embodiment of the invention, there is disclosed an eyedrop bottle holder with resilient arms constructed of: an inverted U-shaped band made from resilient injection molded plastic. The top middle portion of the inverted U-shape band includes a centrally located opening through which the top (dispensing portion) of a standard eyedrop bottle containing eyedrop solution may be positioned and held. The right and left arms of the U-shape band each terminate in an outwardly disposed J-shape foot, the underside of which is covered by a soft rubber-like pad. When a user inserts a standard eyedrop bottle into the holder, the dispensing tip of the eyedrop bottle may be positioned in close proximity to the user's eye. In this manner, the user may cause his or her eye lid to remain open by using the fingers of one hand to squeeze the right and left arms of the holder together, then placing the rubber-like pad of one arm on his or her upper ridge of the orbital eye socket and the rubber-like pad of the second arm on the lower ridge of his or her orbital eye socket, and then releasing the arms thereby causing the skin of the user's upper and lower eyelids to be spread apart from each other and remain spread during an eyedrop solution dispensing event.

In a preferred embodiment of the invention the eyedrop bottle is retained within a housing. The housing includes an electromechanical assembly that includes a rotating cam member that pushes on the side of the bottle until a predetermined amount of solution is dispensed. When a set amount of eyedrop solution has been dispensed, the assembly resets itself automatically to prepare for the next dispensing event. An electronic sensor detects the passage of a drop of solution from the bottle and thereby directs a reverse motion to the rotating cam member. Mechanical and/or electronic tilt sensors assist the user in properly orienting the device for use. An adaptor may be used to accommodate non-standard sized eyedrop bottles.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Figure 1:
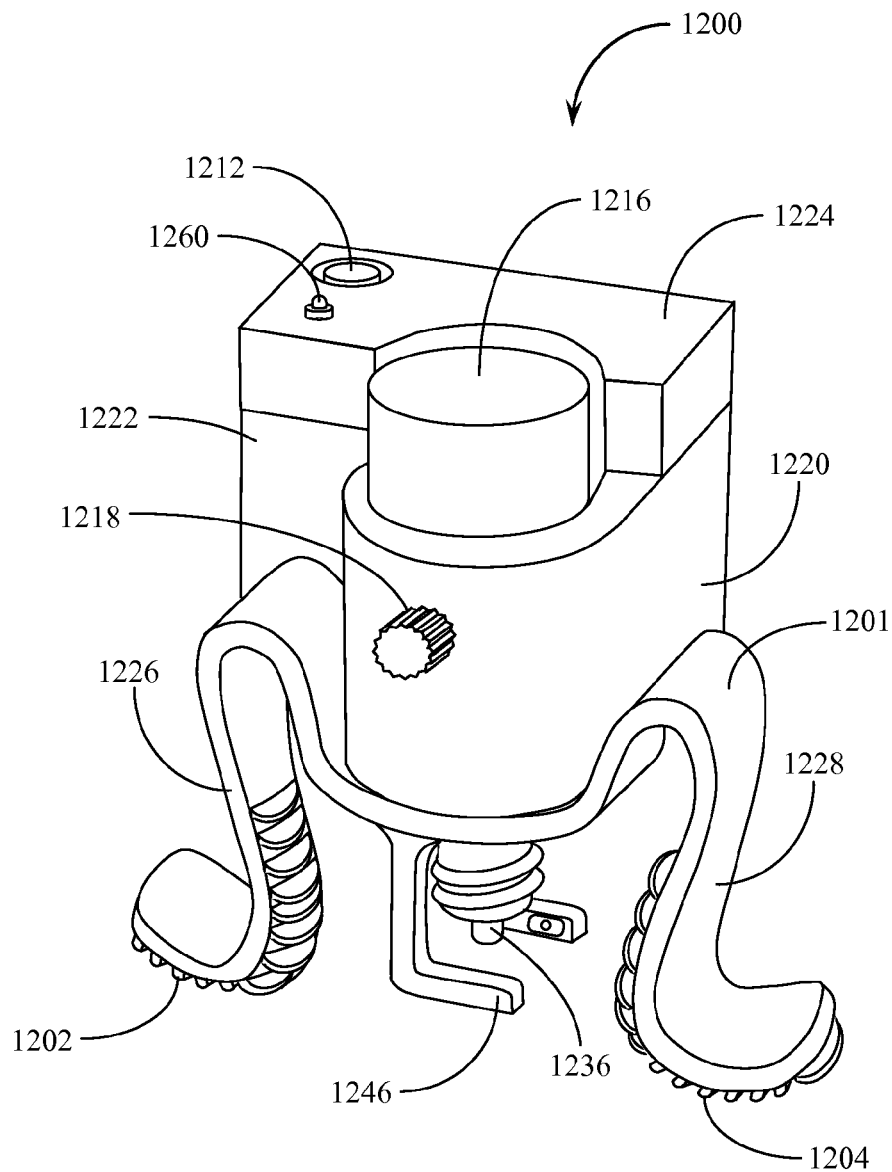
FIG. 1 is a perspective view of a first preferred embodiment of the present invention shown assembled with an eyedrop bottle (minus its cap) fixed within the device.

Reference is made first to FIG. 1 for an overview description of the eyedrop delivery system of the present invention. FIG. 1 is a perspective view of a first preferred embodiment of the present invention shown assembled with an eyedrop bottle fixed within the device. Eyedrop delivery system 1200 is shown to comprise an enclosure assembly made up primarily of front housing 1220, rear housing 1222, and housing top 1224. A standard sized eyedrop bottle 1216 is positioned within a cylindrical extension of front housing 1220. Eyedrop bottle 1216 may be fixed in position with adjustment screw 1218 directed through the wall of the cylindrical extension of front housing 1220. Bottle tip nozzle 1236 extends downward in the view of FIG. 1 and is shown with the cap removed to allow for dispensing of the eyedrop solution.

The housing components described above for the eyedrop delivery system 1200 of the present invention are positioned on eyelid retracting assembly 1201. This assembly is comprised of a unitary curved band of resilient, semi-rigid, plastic material that serves to support the housing components (in conjunction with eyedrop bottle 1216) and further to facilitate the retention of the eye in an open condition ready to receive the drop of eyedrop solution. Eyelid retracting assembly 1201 accomplishes this by providing flexible but resilient arms that terminate in soft cushioned feet that are positioned on the upper and lower orbital rim sites around the user's eye.

Lower flex arm 1226 and upper flex arm 1228 extend from a common point of attachment to the housing components of eyedrop delivery system 1200. Each flex arm 1226 and 1228 extends downward to terminate in a "J" shaped eyelid retracting leg. Lower eyelid retracting leg 1202 terminates lower flex arm 1226, while upper eyelid retracting leg 1204 terminates upper flex arm 1228. As shown, each of the eyelid retracting legs 1202 and 1204 are covered on one face with soft resilient cushion material so as to gently engage the skin of the user at the upper and lower orbital sites against which the device and delivery system is placed (see FIG. 10).

As used herein, the terms upper and lower refer to positions about the eye of the user; upper referring to the area about the eyebrow, and lower referring to the area about the top part of the cheek. The upper curved sections of eyelid retracting assembly 1201, on either side of front housing 1220, provide the necessary spring resiliency to eyelid retracting assembly 1201 so as to allow the user to squeeze the upper and lower eyelid retracting legs 1202 and 1204 together for placement of the device against the face about the eye and thereafter release the legs slightly so as to allow for the expansion of eyelid retracting assembly 1201 and the corresponding opening of, or retention of the open condition of, the eye.

Various electronic components are associated with the operation of eyedrop delivery system 1200 as described in more detail below. In the view of FIG. 1, activation button 1212 is shown as a recessed button positioned on housing top 1224. Also positioned on housing top 1224 is a low battery LED 1260 which provides an indication to the user that the internal battery (rechargeable or replaceable) is low and should be replaced or recharged. Also shown as extending down from eyelid retracting assembly 1201 is drop sensor assembly 1246 which is shown to include opposing legs that bracket bottle tip nozzle 1236. The manner of the operation of the drop sensor assembly 1246 in conjunction with the activation of the device is described in more detail below.

Figure 2:
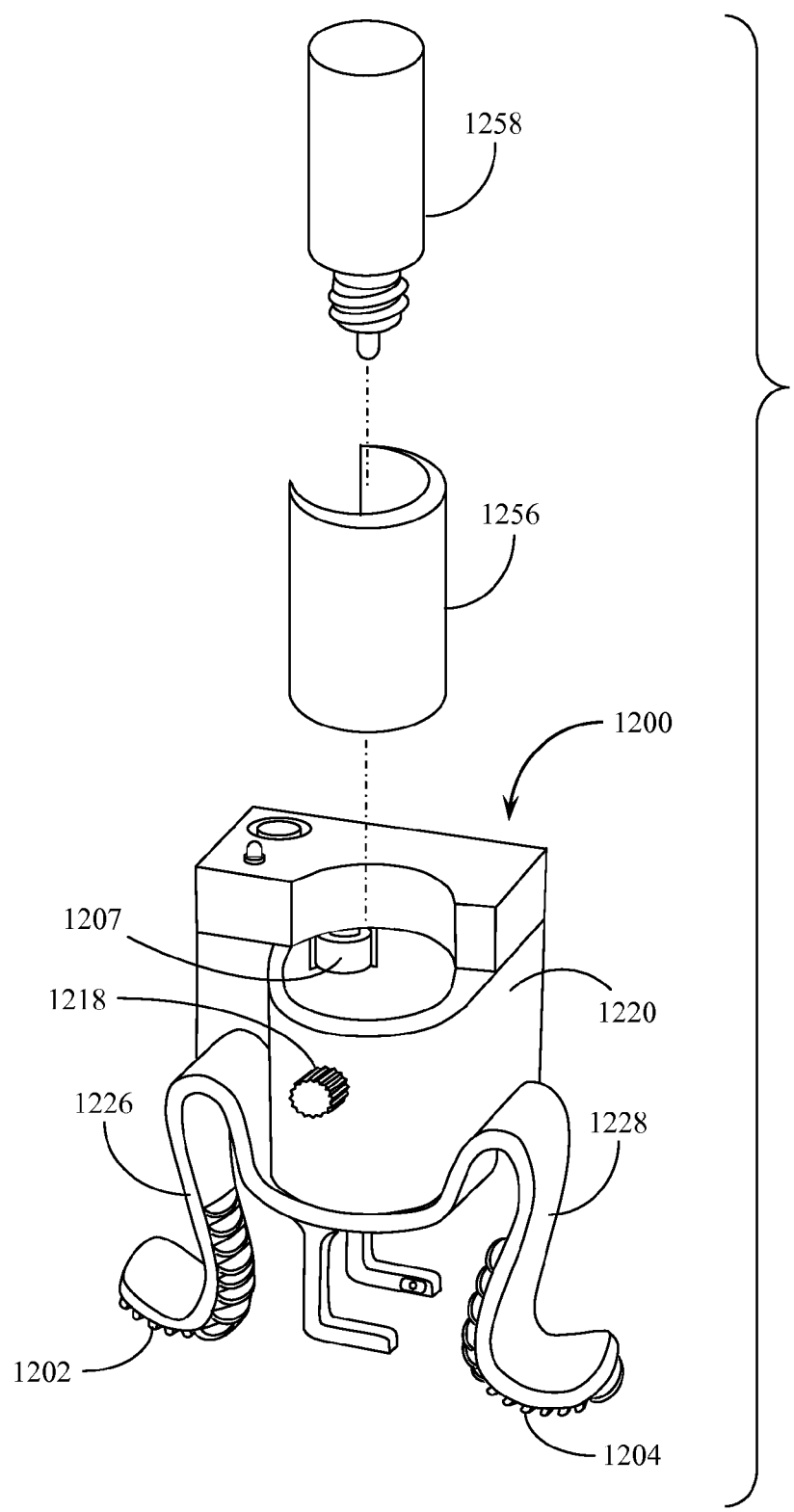
FIG. 2 is an exploded perspective view of the first preferred embodiment of the present invention shown with the eyedrop bottle removed and configured with a bottle size adaptor.

Reference is next made to FIG. 2 for a brief description of an additional optional component to the system of the present invention for adaptation of the device to an alternate sized eyedrop bottle. Eyedrop delivery system 1200 is shown in FIG. 2 with the eyedrop bottle removed. In this view, dispensing cam assembly 1207 can be seen within the confines of the cylindrical housing component of the device. In the preferred embodiment of the present invention, the dimensions of the cylindrical enclosure established by front housing 1220, appropriately accommodates a standard sized eyedrop bottle (typically a 15 ml or 0.5 oz. squeeze bottle).

Some variation of the outer diameter of such standard sized bottles may be accommodated through the use of adjustment screw 1218. Significant departures from a standard sized diameter bottle may be addressed through the use of bottle size adapter 1256 as shown in FIG. 2. This partial cylindrical sleeve may be inserted into the cylindrical opening of front housing 1220 as shown, thereby directing alternate sized eyedrop bottle 1258 towards the side of front housing 1220 where it is positioned adjacent to dispensing cam assembly 1207. The manner in which dispensing cam assembly 1207 squeezes the eyedrop bottle is described in more detail below. Eyedrop delivery system 1200 however is structured the same as the system shown in FIG. 1 and is thereby adaptable to a variety of eyedrop bottle sizes.

Figure 3:
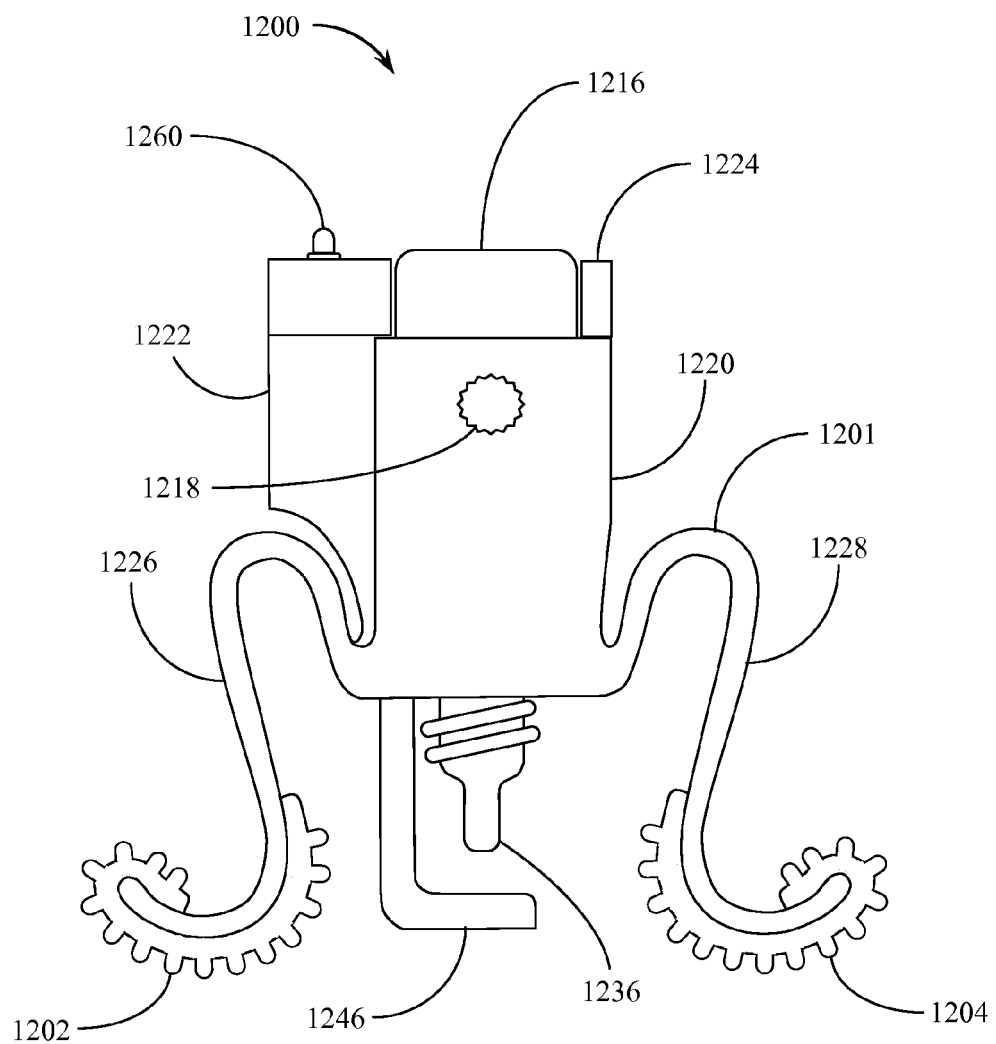
FIG. 3 is a front side elevational view of the first preferred embodiment of the present invention shown assembled with an eyedrop bottle fixed within the device.

Reference is next made to FIG. 3 for a detailed description of a front side elevational view of the first preferred embodiment of the present invention shown assembled with an eyedrop bottle fixed within the device. In this view, the same components as shown generally in FIG. 1 may be seen. Eyedrop delivery system 1200 is shown to be generally comprised of front housing 1220, rear housing 1222, and housing top 1224. Eyedrop bottle 1216 is positioned within front housing 1220 with bottle tip nozzle 1223 extending below the housing between lower flex arm 1226 and upper flex arm 1228.

Lower flex arm 1226 is shown to include lower eyelid retracting leg 1202, at least partially covered with a resilient soft cushion material appropriate for engagement with the skin about the orbital socket of the eye of the user. Likewise, upper flex arm 1228 is shown to include upper eyelid retracting leg 1204 with a similar soft cushion covering. Extending below front housing 1220 is drop sensor assembly 1246. Sensor assembly 1246 is positioned to sense the passage of a drop of solution from eyedrop bottle 1216 by way of bottle tip nozzle 1236 downward (in the orientation shown in FIG. 3) and preferably into the eye of the user.

Drop sensor assembly 1246 may preferably be comprised of two "L" shaped legs that extend down from front housing 1220 below eyelid retracting assembly 1201 so as to be appropriately positioned below bottle tip nozzle 1236 to sense the passage of a drop of solution. As described in more detail below, drop sensor assembly 1246 is preferably the combination of a photodiode and a photo sensor, each positioned on one of the two "L" shaped legs of the assembly. Electrical conductors extend within the "L" shaped legs of the assembly up into the enclosure defined by the housing components of the eyedrop delivery system 1200. In general, a single pair of conductors may extend to the photodiode and a similar single pair of conductors to the photo sensor and are sufficient to provide the necessary electronics connections associated with operation of drop sensor assembly 1246.

Also seen in FIG. 3 is a manner of integrating the construction of eyelid retraction assembly 1201 into front housing 1220 of the eyedrop delivery system 1200. Although the various components of the overall eyedrop delivery system 1200 may be constructed from individual sections of molded material (preferably rigid or semi-rigid plastic material), it may be preferred to mold the eyelid retracting assembly 1201 as a unitary component with front housing 1220 as shown in FIG. 3. Alternately, these components may be molded separately and attached one to the other as shown in FIG. 1.

Figure 4:
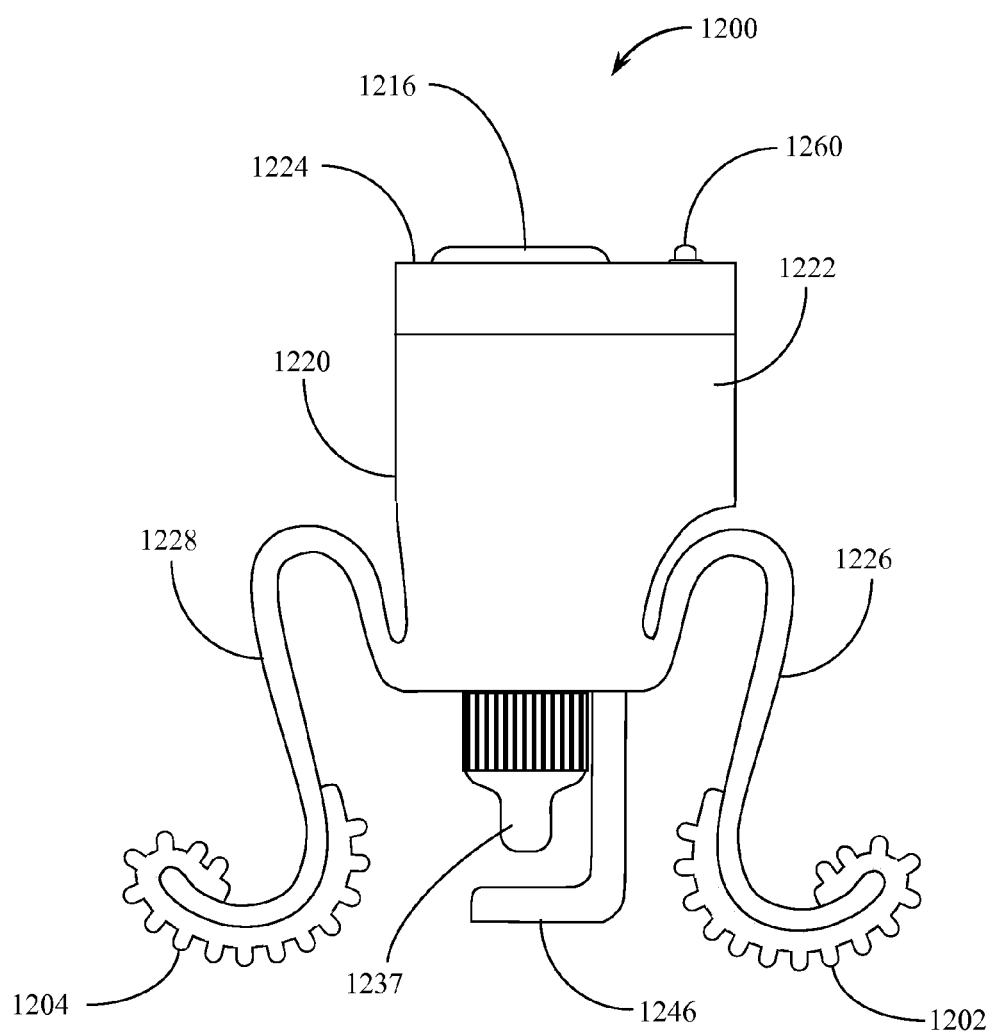
FIG. 4 is a back side elevational view of the first preferred embodiment of the present invention shown assembled with an eyedrop bottle fixed within the device.

Reference is next made to FIG. 4 for a detailed description of the obverse view of the device shown in FIG. 3. In the view of FIG. 4, the backside of the housing components can be seen. In this view, front housing 1220 is seen to transition into rear housing 1222 across the back of the eyedrop delivery system 1200. Housing top 1224 is shown to extend across both front housing 1220 and rear housing 1222. Front housing 1220 is primarily descriptive of the cylindrical portion of the device designed to receive the eyedrop bottle as shown in FIG. 3. FIG. 4 also discloses the manner in which bottle cap 1237 may be returned to the top of bottle 1216 while it remains held in eyedrop delivery system 1200.

Figure 5:
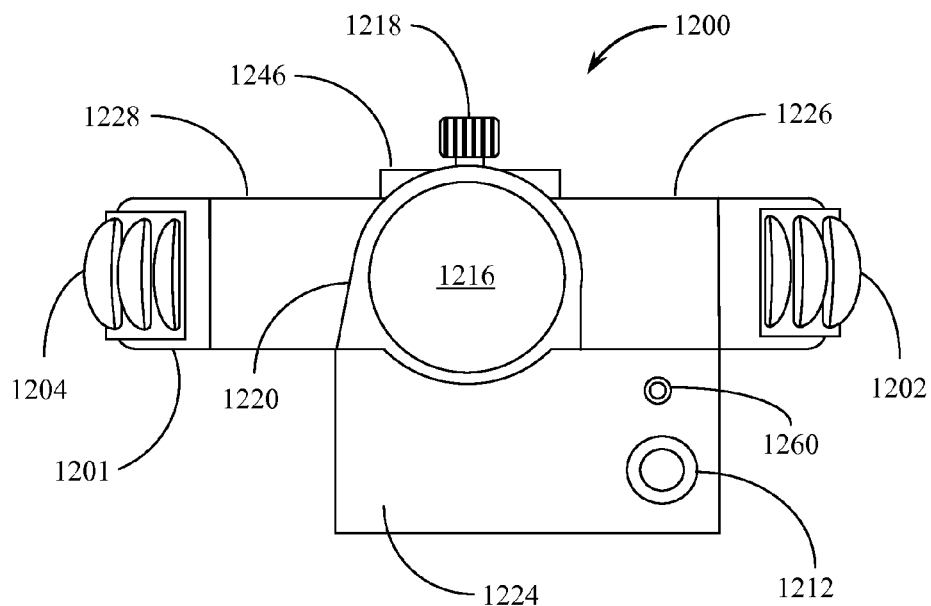
FIG. 5 is a top plan view of the first preferred embodiment of the present invention shown assembled with an eyedrop bottle fixed within the device.
Figure 6:
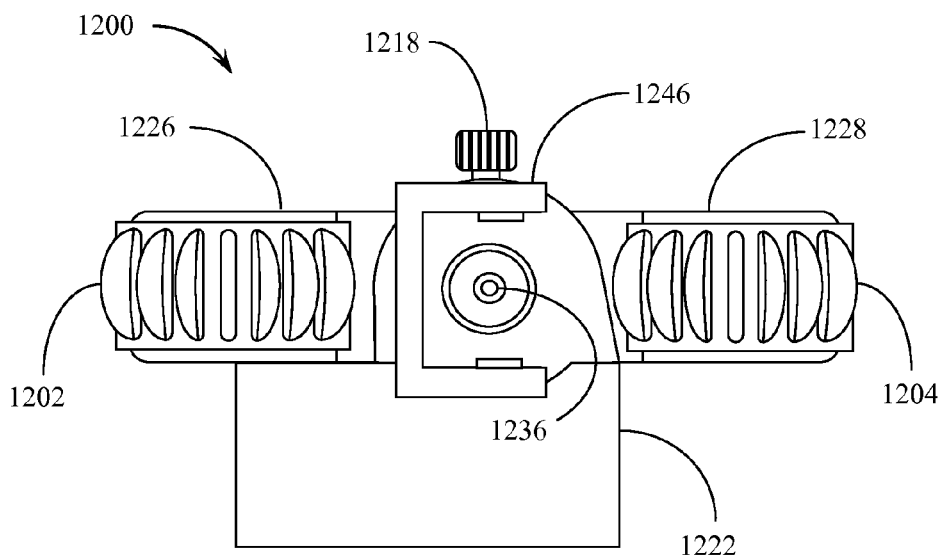
FIG. 6 a bottom plan view of the first preferred embodiment of the present invention shown assembled with an eyedrop bottle fixed within the device.

Reference is next made to FIGS. 5 and 6 which are a top plan view and a bottom plan view respectively of the first preferred embodiment of the present invention shown assembled with an eyedrop bottle fixed within the device. FIG. 5 represents a top view, which shows eyedrop bottle 1216 centrally (co-axially) positioned within the cylindrical extension of front housing 1220. On either side of front housing 1220, enclosing eyedrop bottle 1216, are lower flex arm 1226 and upper flex arm 1228. These flex arm components of eyelid retracting assembly 1201 are shown to extend into lower eyelid retracting leg 1202 and upper eyelid retracting leg 1204, each covered with soft resilient cushion components as described above.

Housing top 1224 of eyedrop delivery system 1200 is shown in FIG. 5 to include recessed activation button 1212 as well as low battery LED indicator 1260. Adjustment screw 1218 is shown positioned through the cylindrical wall of front housing 1220 so as to engage the outer diameter wall of eyedrop bottle 1216. A small portion of drop sensor assembly 1246 is visible in FIG. 5 positioned as it is below the front cylindrical wall of front housing 1220.

FIG. 6 is the obverse view of the device shown in FIG. 5, seen from below as the user might view the device immediately prior to use. In this view, drop sensor assembly 1246 is seen in its entirety and is shown to be generally aligned with bottle tip nozzle 1236 so as to provide an accurate indication of the passage of a drop of solution down from bottle tip nozzle 1236 between the two legs of drop sensor assembly 1246. In the preferred embodiment, the photodiode and the photo sensor that make up drop sensor assembly 1246 have a sufficient range of detection so as to identify the passage of a drop of solution even if the drop falls slightly off-center from the bottle tip nozzle 1236. The drop sensor assembly 1246 may therefore accommodate slight deviations from a direct alignment between bottle tip nozzle 1236 and the electronic components associated with drop sensor assembly 1246.

Also seen in FIG. 6 are the fully cushioned surfaces of lower eyelid retracting leg 1202 and upper eyelid retracting leg 1204. The cushioned surfaces of eyelid retracting legs 1202 and 1204 are structured so as to softly engage the skin of the user in the area about the orbital socket around the user's eye with a sufficient friction as to facilitate the retention of the skin and the associated eyelid areas of the user in an open condition. The material should be soft enough to prevent abrasion or other negative impacts to the skin while at the same time having a sufficiently frictional characteristic to prevent the skin from sliding under the surface of the retracting legs. In the view shown in FIG. 6, the preferred embodiment of the present invention is shown to include an array of soft but resilient fins that provide the necessary surface area to prevent slippage of the retracting legs 1202 and 1204 over the skin surface. At the same time, this construction provides a soft surface for contact with the skin of the user.

Figure 7A:
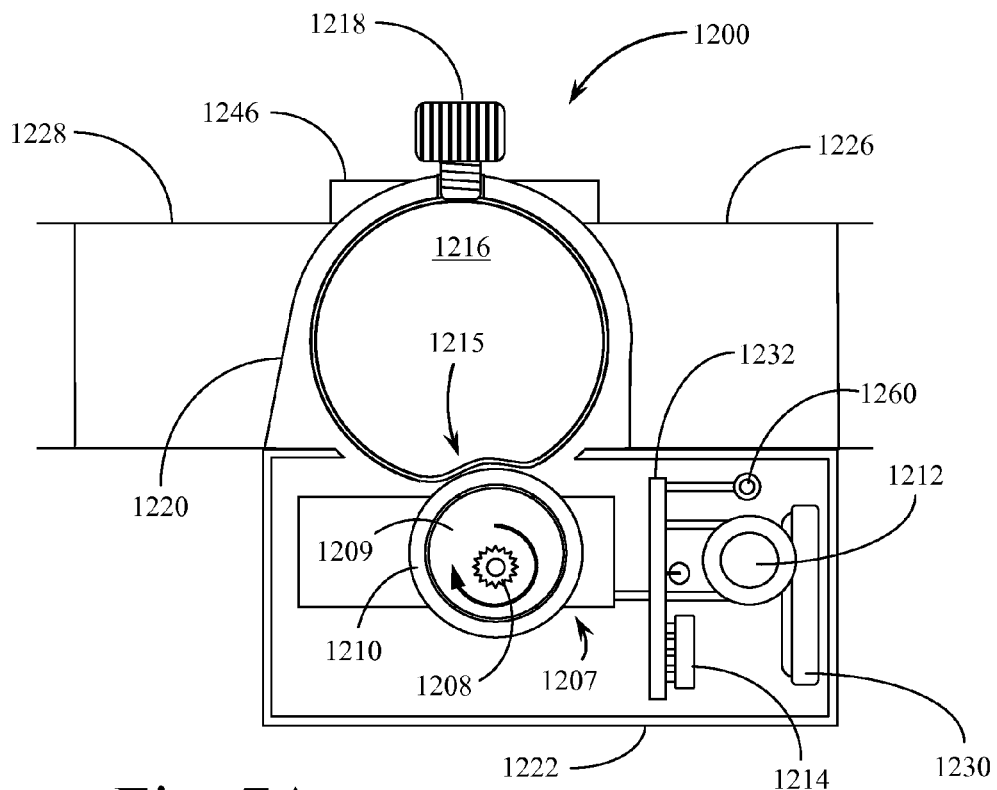
FIGS. 7A & 7B are partial cross sectional views of the device of the present invention showing the interior electromechanical components that direct the movement of the rotating cam into the side of the eyedrop bottle to dispense a drop of solution.
Figure 7B:
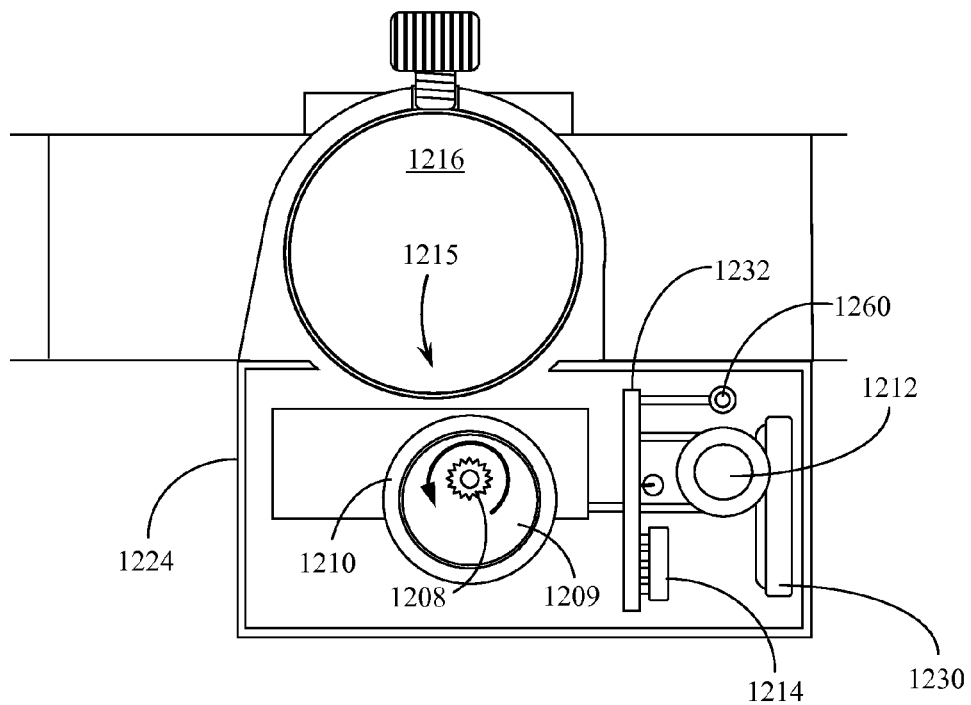

Reference is next made to FIGS. 7A and 7B for a more detailed description of the interior electromechanical components associated with the operation of the eyedrop delivery system of the present invention. FIGS. 7A and 7B provide top plan views of eyedrop delivery system 1200 with the housing top (1224 in the previous figures) removed so that the interior components of the system are disclosed. In FIG. 7A eyedrop delivery system 1200 is shown in the same basic view as that of FIG. 5 with the top of the housing removed for clarity and with the eyelid retracting assembly only partially shown, again for clarity. Eyedrop bottle 1216 is shown positioned within front housing 1220 held in place in part with adjustment screw 1218. On either side of front housing 1220 are lower flex arm 1226 and upper flex arm 1228. Below flex arms 1226 and 1228 may be seen a portion of drop sensor assembly 1246.

Within the enclosure defined by front housing 1220 and rear housing 1222 are shown the various components that carry out the automated operation of the system. These components include dispensing cam assembly 1207 and the associated electronics used to direct the operation of the cam assembly. The operation of the device of the present invention involves the controlled rotation of an offset cam that may alternately be directed into (FIG. 7A) the side of the flexible eyedrop bottle 1216 or removed from (FIG. 7B) contact with the side of the eyedrop bottle.

Dispensing cam assembly 1207 generally comprises three components and is associated with an electric motor (hidden from view in FIG. 7A) that drives a shaft 1208 in an off center position within inside cylinder 1209 of roller bearing 1210. As motor shaft 1208 turns, it in turn rotates inside cylinder 1209 of offset roller bearing 1210 such that rotational movement of the inside cylinder portion of the bearing does not necessarily effect rotational movement of the external cylinder portion of the roller bearing. In this manner, the offset cam assembly 1207 may alternately direct the external cylindrical portion of bearing 1210 into the side of eyedrop bottle 1216 at wall section 1215 of the eyedrop bottle. Further rotation (or preferably, reverse rotation) of the cam assembly, as directed by the electric motor, rotates offset roller bearing 1210 away from contact with wall portion 1215 of eyedrop bottle 1216 as shown in FIG. 7B.

The electronics associated with the control of the electric motor directing the operation of dispensing cam assembly 1207 are also shown in FIGS. 7A and 7B. In the representation shown, the various primary components of the electronics are shown. These include battery 1230, activation button 1212, PC board 1232, and microprocessor 1214. Activation button 1212 is electrically connected to PC board 1232 as are microprocessor 1214, and battery 1230. Additionally, low battery LED 1260 is shown connected to PC board 1232. Other components typically associated with such control circuitry may be included on PC board 1232 as known in the electronics art according to functions of the system controlling the DC motor associated with dispensing cam assembly 1207.

Although the system of the invention is designed to be operated using battery power from a relatively small DC cell, the battery itself may be either a replaceable battery or a rechargeable battery. Alternate embodiments may provide battery door access into the enclosure if a replaceable battery is included, while charging circuit components and a charger connector (see FIG. 12) may be included if a rechargeable battery system is utilized.

Figure 8:
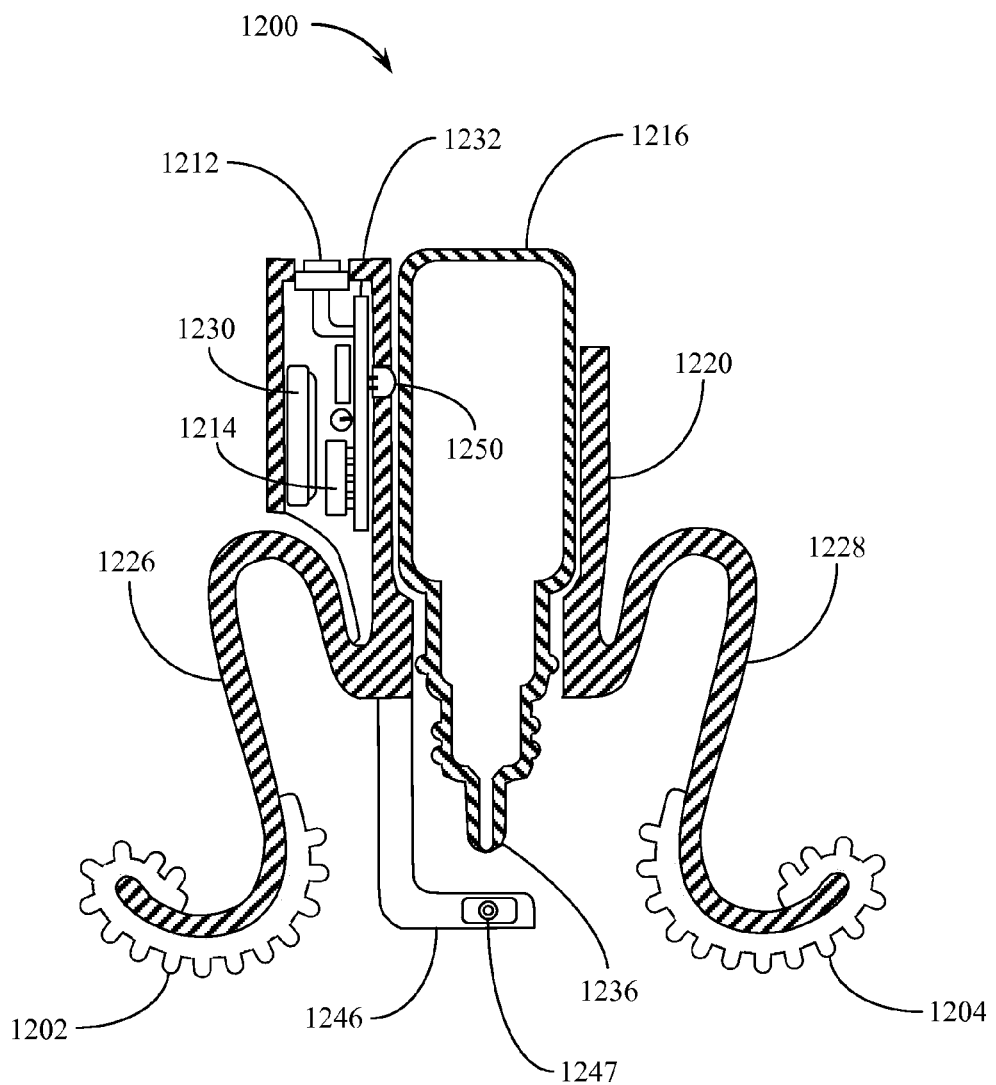
FIG. 8 is a front (lateral) cross sectional view of the first preferred embodiment of the present invention showing the internal electronic components operable for the control of the device.

Reference is next made to FIG. 8 for a cross-sectional view of eyedrop delivery system 1200 of the present invention showing in an elevational view the various structures of the device as seen generally across a lateral diameter of the eyedrop bottle 1216. In this view of FIG. 8, the interior of eyedrop bottle 1216 can be seen and the placement of the bottle within front housing 1220 with the specific downward orientation of eyedrop bottle 1216 can also be seen. In the partial cross-sectional view shown in FIG. 8, one-half of drop sensor assembly 1246 is shown, in this case with photodiode 1247 directing the beam across the path of a drop that would be dispensed from bottle tip nozzle 1236. The flex arms 1226 and 1228 are also shown in this view integrally constructed from the material and components making up front housing 1220 of the device. Lower eyelid retracting leg 1202 and upper eyelid retracting leg 1204 are also shown in this cross-sectional view.

The interior components described briefly above in conjunction with FIGS. 7A and 7B are shown further in FIG. 8. Battery 1230 is shown positioned in a manner generally parallel to PC board 1232. Various components are shown attached to PC board 1232 including microprocessor 1214 and activation button 1212. Low battery LED 1260 has been omitted for clarity in this view. Also shown in FIG. 8 is an optional electronic component mounted through the wall of front housing 1220 between PC board 1232 and the positioned placement of eyedrop bottle 1216. This optional component is an electronic barcode reader that optically scans a barcode positioned as a label on eyedrop bottle 1216, identifying the product contained within the eyedrop bottle as it is inserted into the device. Controlled by programming within microprocessor 1214, optical reader 1250 may be used to assist in the control of the dispensing of eyedrop solution from the eyedrop bottle according to the requirements for a specific product. The initial optical scan may also be utilized to estimate the remaining amount of solution present in the bottle, and in some instances to control the manner in which the dispensing of a drop is directed by the mechanical components of the system. A wide range of additional control features may be facilitated by information scanned from a barcode positioned on eyedrop bottle 1216.

Figure 9:
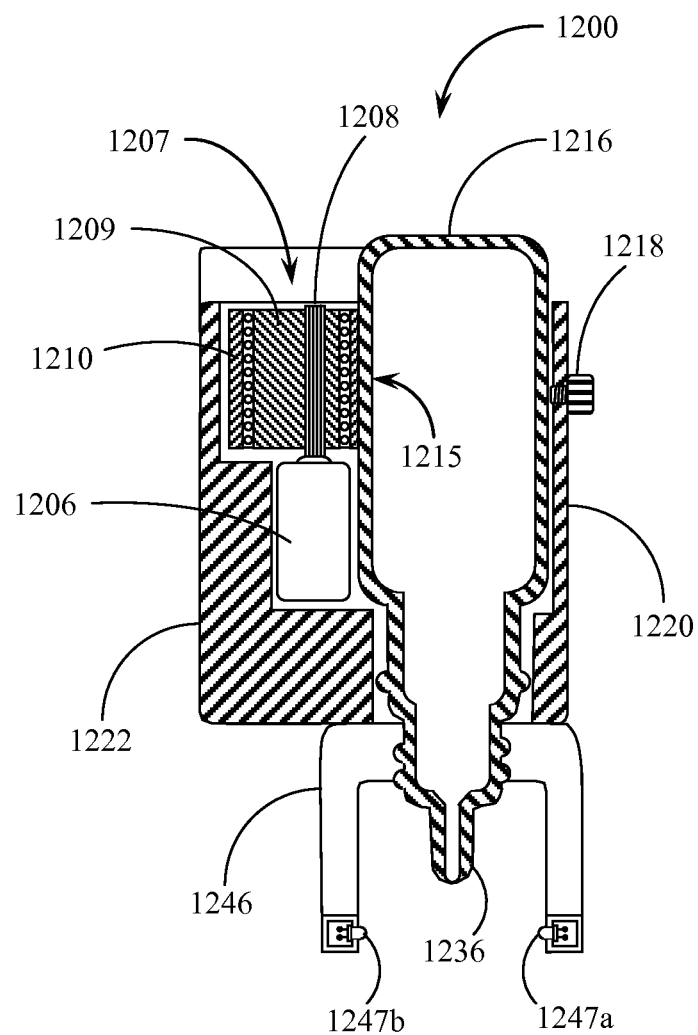
FIG. 9 is a side (transverse) cross sectional view of the first preferred embodiment of the present invention showing the internal electromechanical components operable for the control of the device.

Reference is next made to FIG. 9 which is a further cross-sectional view taken through the device at a view orthogonal to that shown in FIG. 8. In FIG. 9 the mechanical components of the system are shown positioned as they are primarily within rear housing 1222. In the view of FIG. 9, eyedrop bottle 1216 is shown positioned within the cylindrical wall of front housing 1220 adjacent the components of dispensing cam assembly 1207. With the orientation shown in FIG. 9 dispensing cam assembly 1207 is positioned as it might be turned as in FIG. 7B, that is withdrawn from wall section 1215 of eyedrop bottle 1216, before or after having been pinched or squeezed inward as in the view of FIG. 7A. As can be seen in FIG. 9, however, rotation of dispensing cam assembly 1207 will direct the larger radius of the dispensing cam assembly into wall section 1215 of eyedrop bottle 1216 so as to squeeze the bottle and dispense a drop of eyedrop solution.

As briefly described above, dispensing cam assembly 1207 is primarily constructed of electric motor 1206 having motor shaft 1208 which extends up through internal cylinder 1209 of offset roller bearing 1210. Since motor shaft 1208 is positioned on an offset axis of internal cylinder 1209 of roller bearing 1210, rotation of the bearing directs the larger radius portion into the wall of eyedrop bottle 1216. Because of the cylinder-within-a-cylinder construction of offset roller bearing 1210, the outer surface of the external portion of the bearing need not rotate abrasively against the wall of eyedrop bottle 1216 as it is pushed in and out from compressive contact with wall section 1215. The internal cylinder 1209 of offset roller bearing 1210 may therefore rotate freely under the control and direction of electric motor 1206 not subject to any rotational friction, while the external cylinder portion of the offset roller bearing 1210 may simply move in and out against the wall of the eyedrop bottle.

Also shown in FIG. 9 are the extended leg components of drop sensor assembly 1246. In this view, photodiode 1247*a* is shown in an orientation opposing photo sensor 1247*b* across the path that a drop would fall after exiting from bottle tip nozzle 1236 as described above. Photodiode 1247*a* emits electromagnetic waves and photo sensor 1247*b* receives the emitted electromagnetic waves. Because the photodiode and photo sensor are positioned diametrically apart from each other across the path of a drop of solution dispensed from the eyedrop bottle, the passage of the drop of solution serves to interrupt the emitted electromagnetic waves in a manner detectable by the photo sensor. Once again, electrical conductors connect photodiode 1247*a* and photo sensor 1247*b* with the associated control electronics described above in conjunction with FIG. 8. Those skilled in the art will recognize that very accurate control of DC motor 1206 may be utilized to correspondingly control the very accurate and specific dispensing of solution from eyedrop bottle 1216. Through the use of drop sensor assembly 1246, the control electronics of the system may very quickly identify when a dispensing event (a single drop) has occurred and immediately withdraw (counter-rotate) the offset cam of dispensing cam assembly 1207 so as to prevent a further drop of solution from being dispensed from the bottle.

Figure 10:
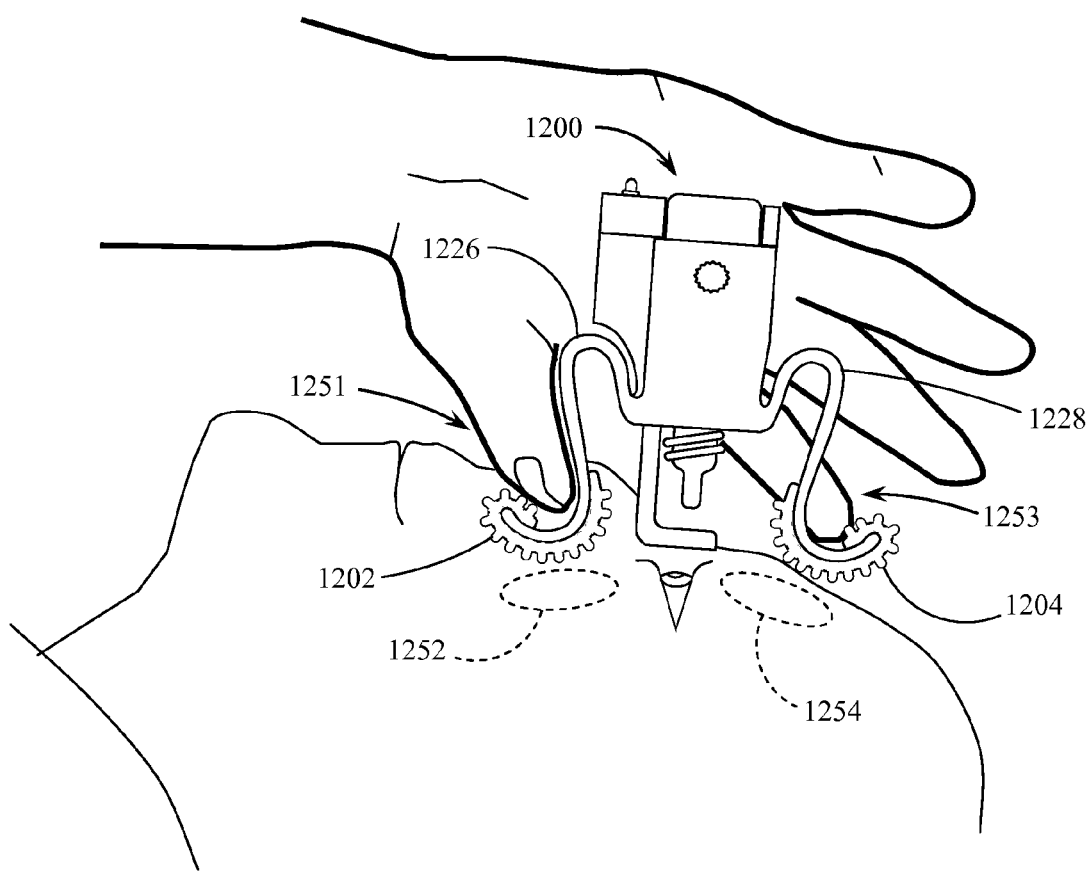
FIG. 10 is a perspective view of a preferred method of use of the device of the present invention.

Reference is now made to FIG. 10 for a description of the manner in which the device 1200 of the invention is utilized in order to accurately dispense a drop of solution into the user's eye. Oriented in the manner shown in FIG. 10, the user holds the device with the thumb 1251 and forefinger 1253 engaging lower flex arm 1226 and upper flex arm 1228 respectively in a manner that allows the user to initially squeeze the arms towards each other and then allow the arms to return to an extended position once the device has been placed against the skin of the user above and below the orbital socket of the eye.

Operation of the device of the present invention is facilitated by the user reclining in a horizontal position as shown in FIG. 10 and holding the device in the right hand as shown with the thumb and forefinger engaging the lower and upper flex arms. As the user holds the device as described above and squeezes the flex arms together, the cushioned surfaces of lower eyelid retracting leg 1202 and upper eyelid retracting leg 1204 are placed into contact with the skin of the user above 1254 and below 1252 the orbital socket just outside of the eyelid portion of the skin surrounding the eye. Once in contact with the skin's surface, the user then gently loosens the compressive force between the thumb and forefinger, all the while keeping the device engaged against the skin. This action of releasing the compressive force allows the eyelid retracting assembly 1201 to spring back to its original configuration with flex arms 1226 and 1228 moving outward. As the lower and upper flex arms move outward, while the eyelid retracting legs remain in gentle contact with the skin of the user about the eye, the eyelids are opened further and/or are retained open by the outward force exerted by the flex arms tending to return to their original configuration. In this manner, the device of the present invention imitates the action of a user that might utilize a thumb and forefinger to hold open the eyelids around the eye while a drop is being dispensed. This use of the present device, however, allows the user a free hand to actually control the dispensing of the eyedrop rather than being required to hold open the eye with one hand in a typically inadequate manner.

The device of the present invention is configured in a sufficiently compact form as to allow the user to push the activation button on the device with the hand that is holding the device or, given a free hand, to push the activation button with the user's other hand. In either case, once properly positioned and oriented, the user pushes the activation button and causes the device to accurately dispense a single drop of solution into the eye while the eyelids are being retained in an open position by way of the spring force in the flex arm components. Drop sensor assembly 1246 shown in FIG. 10 then detects the passage of a drop from the dispensing device into the user's eye and then reverses the motion of the internal mechanisms associated with the automatic dispensing device as described above.

Drop sensor assembly 1246 is of course positioned so as to prevent any direct contact between the assembly and the user's eye. The placement and positioning of the eyedrop bottle within the eyedrop delivery system also positions the dispensing tip of the bottle appropriately apart from the surface of the user's eye. The resiliency associated with eyelid retracting assembly 1201 directs flex arms 1226 and 1228 horizontally apart or together rather than significantly changing the distance to the eye.

Figure 11:
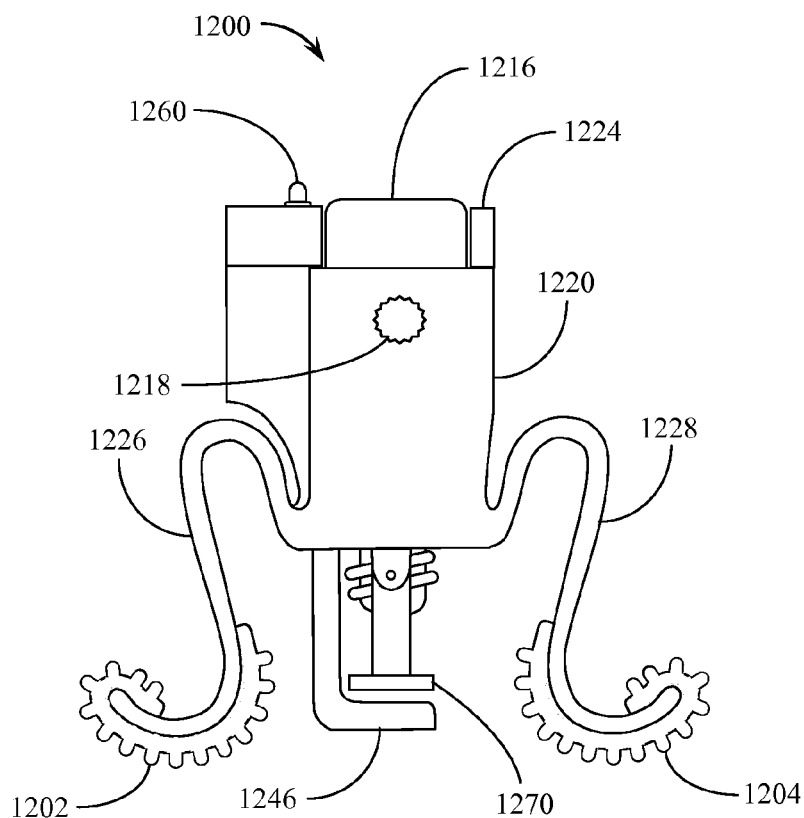
FIG. 11 is a front side elevational view of an alternate embodiment of the present invention with a mechanical tilt indicator.

Reference is next made to FIG. 11 for a brief description of an alternate optional feature that may be incorporated into the device of the present invention. FIG. 11, which generally represents the same view as that shown in FIG. 3, discloses the use of a tilt ring 1270 positioned between drop sensor assembly 1246 and the base of the housing components of the device. Tilt ring 1270 is a pivoting structure that allows the user to recognize when the entire assembly is at the proper angle for dispensing. That is, when the dispensing tip 1236, as viewed by the user, is positioned in the center of tilt ring 1270 (as in the side view shown in FIG. 11), a person using the device would know that proper orientation has occurred. The user may tilt or orient the device so that ring 1270 can be seen to be in line with the sensor elements on drop sensor assembly 1246. Indicia may be placed on the bottom of the two "L" shaped legs of drop sensor assembly 1246 to facilitate this alignment.

Figure 13:
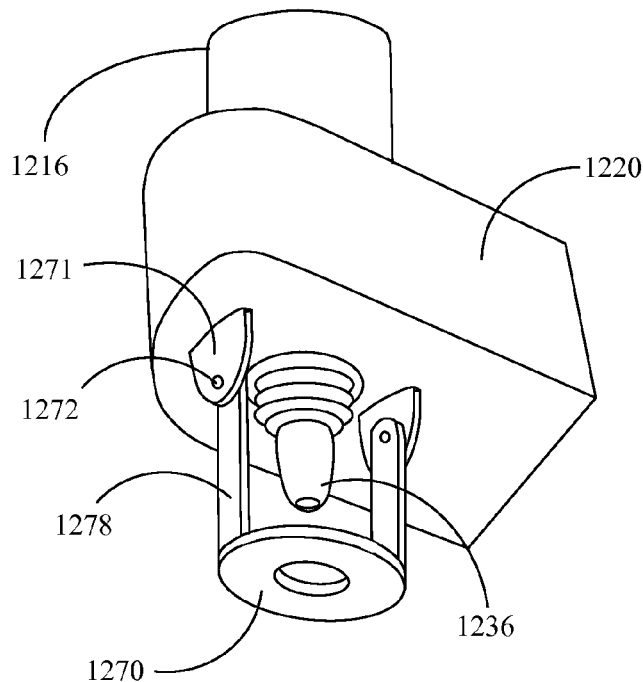
FIG. 13 is a detailed perspective view of the alternate embodiment shown in FIG. 11 with a mechanical tilt indicator.

Reference is now made to FIG. 13, which is a detailed perspective view of the tilt ring component 1270 shown with most of the balance of the components of the device removed for clarity. In this view, ring 1270 can be seen positioned directly under dispensing tip 1236. If the user's head is not tilted back to the proper angle, (again, ideally parallel to a ground plane for the purpose of utilizing gravity to direct the eyedrop into the user's eye) ring 1270 will swing above or below the coaxial orientation in a manner that is identifiable to the user.

Figure 12:
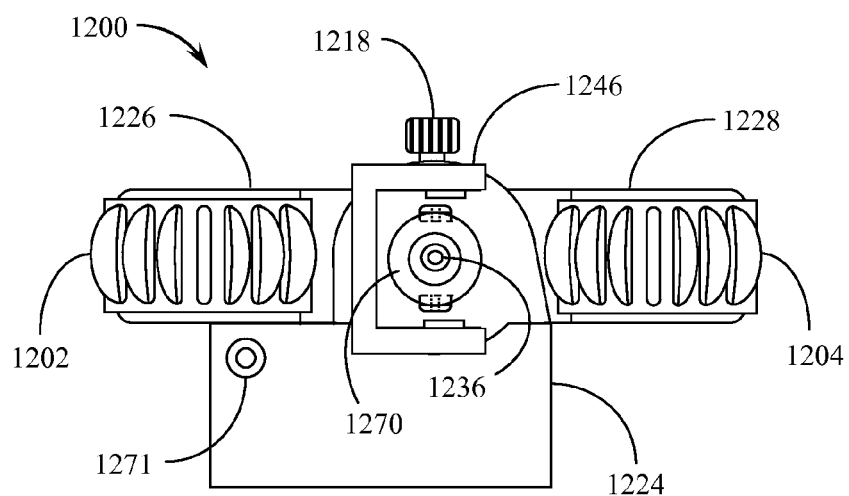
FIG. 12 is a bottom plan view of an alternate embodiment of the present invention with a mechanical tilt indicator and an optional battery recharging connector.

FIG. 12 provides a bottom plan view of the device of the present invention showing the use of the tilt ring 1270 as well as the incorporation of a further optional feature utilized when a rechargeable battery is used within the system. In this view, electrical jack 1271 is shown positioned through a lower wall of the rear housing 1222 of the device in a manner that allows the user to connect an adaptor plug to the device so as to receive an electrical current from an AC adaptor that would recharge the internal rechargeable battery through on board charging circuitry.

Figure 14:
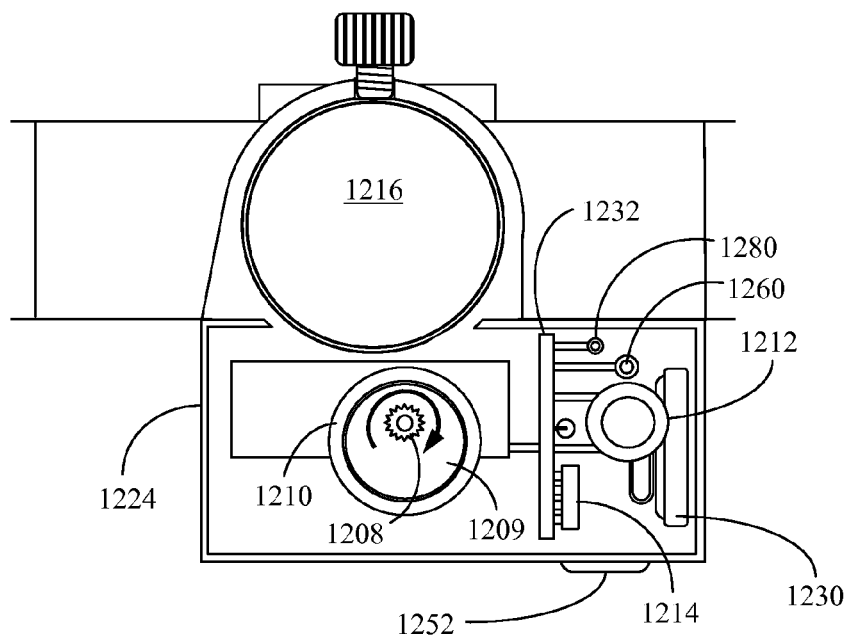
FIG. 14 is a detailed partial cross sectional view of an alternate embodiment of the present invention with an electronic tilt sensor.

FIG. 14 shows a further optional component associated with an alternate embodiment of the present invention that may be used to insure that the user can not dispense a drop unless the correct dispensing angle is achieved. In FIG. 14, tilt switch 1280 is shown within the electronics so as to allow electrical power to the dispensing motor only if the device is at the correct angle. A micro-miniature tilt switch (such as those manufactured by Assemtech Company) which has a fifteen degree zone of operation, is appropriate for controlling this functionality. Any other tilt angle will not allow power to flow through the switch and therefore would not allow operation of the device. Switch 1262 may be mounted to PC board 1232 as shown in FIG. 14 and appropriate programming within microprocessor 1214 may be used to direct power through the switch. Alternately, the switch may simply provide power that enables or disables the entire system's operation. In this latter manner, the switch may act as a wake up device, such that when the system is oriented properly, the electronics are activated and operation of the device may occur. It may be preferable to incorporate both the physical mechanical tilt angle mechanism described in FIGS. 11 and 12, as well as the electronic tilt angle mechanism shown in FIG. 14.

Figure 15:
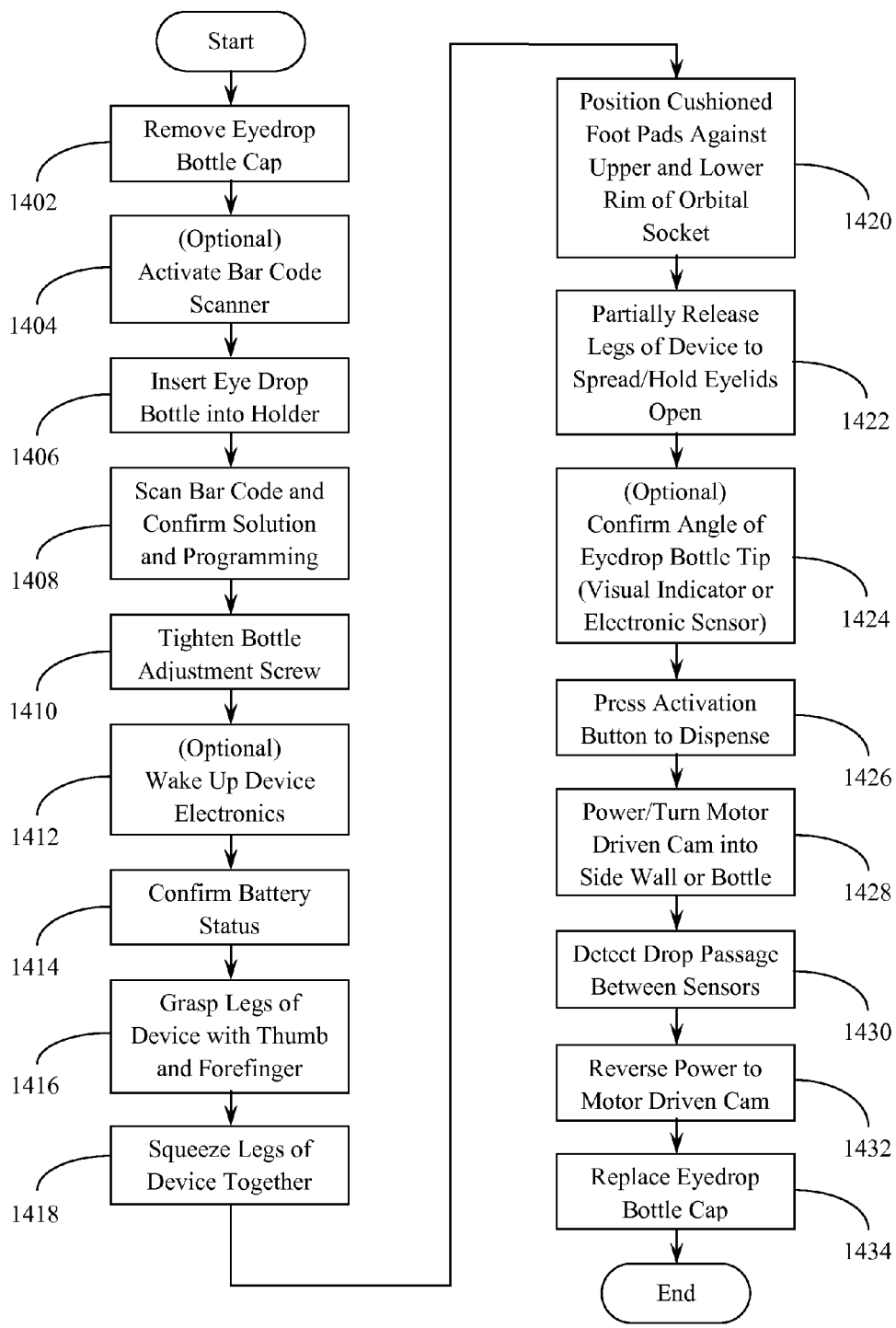
FIG. 15 is a flowchart providing the basic steps in a preferred method of using the eyedrop dispensing device of the present invention.

Reference is finally made to FIG. 15 which provides a flowchart of the basic method steps associated with the operation of the eyedrop dispensing device of the present invention. Provided with the device of the present invention and a typical bottle of eyedrop solution, the user begins the process of using the device by removing the eyedrop bottle cap at Step 1402. This is followed by an optional step of activating a bar code scanner at Step 1404 if the device incorporates such capability and the eyedrop bottle bears a bar code suitable for scanning. The user then inserts the eyedrop bottle into the holder of the device at Step 1406. If bar code scanning has been activated then the system scans the bar code as the bottle is inserted and confirms the solution and programming at Step 1408. The user may then optionally tighten the drop adjustment set screw on the device at Step 1410.

The device is now ready for use and may either be immediately activated or stored with the bottle cap placed back on the bottle while it is in the holder. To initiate use of the device the user proceeds at Step 1412 to wake up the electronics of the system by momentarily touching the activation switch and/or by some other means for powering up the control electronics. Step 1414 involves confirming the battery status as adequate for accurate operation. The user then preferably grasps the device at Step 1416 by placing the thumb and forefinger on the two resilient legs of the device and squeezing the legs together at Step 1418. The user then positions the cushioned pads of the device against the upper and lower rim of the orbital socket about the user's eye at Step 1420.

The user then partially releases the legs of the device at Step 1422 so as to spread and/or hold open the eyelids of the user. During this action the user also may, at Step 1424, confirm the appropriate angle of the eyedrop bottle tip through the use of either a visual mechanical indicator of alignment or through the use of an internal electronic tilt sensor. Once the tilt angle is confirmed, the user presses the activation button at Step 1426 to direct the dispensing of the eyedrop. Meanwhile the resilient legs of the bi-pedal support of the device have maintained the eyelids in an open condition for the ready receipt of the eyedrop accurately into the eye. Pressing the activation button powers the motor to turn the offset cam into the side of the bottle at Step 1428 and thereby compress the bottle and cause it to dispense a drop from the bottle tip.

The system of the present invention then detects the dispensing of the drop of solution from the bottle at Step 1430 and directs the electronic control circuitry to reverse the direction of the motor driven cam at Step 1432. This Step 1430 of detecting the dispensing of a drop of solution includes directing an electromagnetic wave across the path of a dispensed drop and detecting an interruption of the directed electromagnetic wave by a dispensed drop with a diametrically positioned sensor. An example of structures appropriate for carrying out this step in the process are described above with reference to FIGS. 8 & 9. This completes the drop dispensing event which is typically followed by the user replacing the cap on the bottle at Step 1434, preferably while the bottle remains within the device ready for its next use. Variations on the above described process are anticipated depending upon which optional features are provided on the device of the present invention. In its simplest form the process involves using the bi-pedal support to hold the eyelids open and the electromechanical drive motor to automatically compress the bottle to dispense a drop of solution. Additional features as described in the method above contribute to the accuracy and ease with which the device operates.

While the present invention has been described in connection with one or more preferred embodiments, these preferred embodiments are not intended to limit the scope of the invention to the particular forms set forth, but on the contrary, are intended to cover such alternatives, modifications, and equivalents as may be included within the spirit and scope of the invention as defined by the appended claims.

I claim:

1. A device for automatically and accurately dispensing eyedrops into the eye of a user from an eyedrop bottle containing an eyedrop solution, the device comprising:
    (a) a bottle holder and retention assembly;
    (b) a bi-pedal resilient leg support and positioning assembly;
    (c) a movable electromechanical bottle compression assembly comprising:
        (i) a DC electric motor having a rotor shaft extending there from; and
        (ii) a cylindrical bearing cam fixed to the rotor shaft on an axis off-set from the central axis of the cylindrical bearing, the cylindrical bearing cam comprising an internal cylinder fixed to the rotor shaft and an external cylinder slidingly engaged coaxially around the internal cylinder; and
    (d) electronic control circuitry for operational control of the bottle compression assembly;
    wherein the cylindrical bearing cam is positioned within the bottle holder and retention assembly so as to alternately come into contact with the eyedrop bottle when the eyedrop bottle is held and retained within the bottle holder and retention assembly.

2. The device of claim 1 wherein the bi-pedal resilient leg support and positioning assembly is attached to the bottle holder and retention assembly, and comprises:
    (i) an inverted U-shaped band of semi-rigid plastic material defining a middle top aperture through which the eyedrop bottle may be positioned, the inverted U-shaped band comprising first and second arms extending from a middle top portion, the middle top portion attached to the bottle holder and retention assembly;

(ii) first and second J-shaped leg sections extending from the first and second arms respectively, the J-shaped leg sections curving outward and apart at terminal ends thereof; and (iii) cushion pads positioned on the first and second J-shaped leg sections on the outward surfaces of the curved terminal ends thereof.

3. The device of claim 1 wherein the bottle holder and retention assembly comprises:

(i) a cylindrical wall enclosure having first and second open ends for receiving the eyedrop bottle therein and orienting the eyedrop bottle for dispensing the eyedrop solution into the user's eye; and (ii) a dispensing control enclosure for supporting and positioning the movable electromechanical bottle compression assembly and the electronic control circuitry.

4. The device of claim 1 wherein the electronic control circuitry for operational control of the bottle compression assembly comprises:

(i) a battery; and (ii) an activation switch for directing power from the battery to the movable electromechanical bottle compression assembly and thereby directing a compressive motion by the electromechanical bottle compression assembly.

5. The device of claim 4 wherein the battery is rechargeable and the electronic control circuitry further comprises a battery recharge circuit and an external connector for receiving a flow of recharge current into the battery recharge circuit.

6. The device of claim 4 wherein the electronic control circuitry further comprises a dispensed drop sensing assembly, the detection of a dispensed drop directing a de-compressive motion by the electromechanical bottle compression assembly.

7. The device of claim 6 wherein the dispensed drop sensing assembly comprises a photodiode for emitting electromagnetic waves and a photo sensor for receiving the emitted electromagnetic waves, the photodiode and photo sensor positioned diametrically apart from each other across the path of a drop of solution dispensed from the eyedrop bottle, the passage of the drop of solution serving to interrupt the emitted electromagnetic waves in a manner detectable by the photo sensor.

8. The device of claim 1 wherein the bottle holder and retention assembly further comprises a drop adjustment screw positioned in adjustable contact with an external wall of the eyedrop bottle when the eyedrop bottle is positioned within the bottle holder and retention assembly.

9. The device of claim 1 further comprising a tilt control system for facilitating a proper orientation of the device for accurate dispensing of an eyedrop from the eyedrop bottle held within the device.

10. The device of claim 9 wherein the tilt control system comprises a mechanical, gravitationally movable, indicator positioned so as to be viewed by the user during the dispensing of a drop from the eyedrop bottle held within the device.

11. The device of claim 9 wherein the tilt control system comprises a microelectromechanical system (MEMS) device incorporated into the electronic control circuitry for inhibiting activation of the device unless the device is in a proper orientation for accurate dispensing of the eyedrop solution.

12. The device of claim 1 further comprising an eyedrop bottle size adaptor for modifying a size dimension of the bottle holder and retention assembly to receive alternate sized eyedrop bottles.

13. The device of claim 1 wherein the electronic control circuitry further comprises a bar code reader oriented and positioned to read a bar code placed on an exterior wall of the eyedrop bottle.

14. A method for dispensing eyedrops into the eye of a user from an eyedrop bottle containing an eyedrop solution comprising the steps of:

(a) providing a bottle of eyedrop solution, the bottle having a side wall and a cap;

(b) providing an eyedrop dispensing device having an eyedrop bottle holder, a bi-pedal resilient leg support structure with cushion foot pads, a movable electromechanical bottle compression assembly, and an electronic control circuit;

(c) removing the cap of the eyedrop bottle;

(d) inserting the eyedrop bottle into the eyedrop bottle holder;

(e) grasping the legs of the bi-pedal resilient leg support structure between a thumb and a forefinger;

(f) squeezing the legs of the bi-pedal resilient leg support structure together with the thumb and forefinger into a spring-loaded compressed condition;

(g) positioning the cushion foot pads of the resilient leg support structure in its compressed condition against the upper and lower rim of the orbital socket about the eye of the user;

(h) at least partially releasing the legs of the bi-pedal resilient leg support structure to release the support structure from the spring-loaded compressed condition to spread/hold the eyelids of the user open;

(i) confirming an angle of the eyedrop bottle tip to be proper for dispensing a drop of solution into the eye of the user;

(j) activating the electronic control circuit to direct motion of the movable electromechanical bottle compression assembly to compress the eyedrop bottle;

(k) compressing the eyedrop bottle and dispensing a drop of solution there from;

(l) detecting the dispensing of a drop of solution from the eyedrop bottle towards the eye of the user;

(m) de-activating the electronic control circuit to direct a reverse motion of the movable electromechanical bottle compression assembly and to thereby remove compression from the eyedrop bottle; and (n) replacing the cap of the eyedrop bottle.

15. The method of claim 14 further comprising the steps of determining an angle of orientation of the eyedrop bottle prior to dispensing a drop of solution and preventing the dispensing of a drop of solution unless the eyedrop bottle is oriented in a generally vertical alignment with respect to a gravitational force.

16. The method of claim 14 further comprising the steps of reading a bar code affixed to the eyedrop bottle as the bottle is inserted into the eyedrop bottle holder and using the bar code information to at least partially control the dispensing of eyedrops.

17. The method of claim 14 wherein the step of detecting the dispensing of a drop of solution comprises the steps of directing an electromagnetic wave across the path of a dispensed drop and detecting an interruption of the directed electromagnetic wave by a dispensed drop with a diametrically positioned sensor.

18. A device for automatically and accurately dispensing eyedrops into the eye of a user from an eyedrop bottle containing an eyedrop solution, the device comprising:
(a) a bottle holder and retention assembly;
(b) a bi-pedal resilient leg support and positioning assembly;
(c) a movable electromechanical bottle compression assembly; and
(d) electronic control circuitry for operational control of the bottle compression assembly the electronic control circuitry comprising:
(i) a battery;
(ii) an activation switch for directing power from the battery to the movable electromechanical bottle compression assembly and thereby directing a compressive motion by the electromechanical bottle compression assembly; and
(iii) a dispensed drop sensing assembly, the detection of a dispensed drop directing a de-compressive motion by the electromechanical bottle compression assembly.

19. The device of claim 18 wherein the dispensed drop sensing assembly comprises a photodiode for emitting electromagnetic waves and a photo sensor for receiving the emitted electromagnetic waves, the photodiode and photo sensor positioned diametrically apart from each other across the path of a drop of solution dispensed from the eyedrop bottle, the passage of the drop of solution serving to interrupt the emitted electromagnetic waves in a manner detectable by the photo sensor.

* * * * *